(12) United States Patent
McIntyre, IV

(10) Patent No.: US 6,468,226 B1
(45) Date of Patent: Oct. 22, 2002

(54) REMOTE TISSUE BIOPSY APPARATUS AND ASSOCIATED METHODS

(76) Inventor: John J. McIntyre, IV, 18 Hemlock Rd., Hanover, NH (US) 03755

( * ) Notice: Subject to any disclaimer, the term of this patent is extended or adjusted under 35 U.S.C. 154(b) by 0 days.

(21) Appl. No.: 09/721,245

(22) Filed: Nov. 22, 2000

(51) Int. Cl.$^7$ .............................................. A61B 10/00
(52) U.S. Cl. ........................ 600/564; 600/567; 606/167
(58) Field of Search .................................. 600/562, 564, 600/565, 566, 567, 568, 417, 429; 606/130, 167, 170; 378/20; 901/18

(56) References Cited

U.S. PATENT DOCUMENTS

| | | | |
|---|---|---|---|
| 5,053,042 A | 10/1991 | Bidwell | 606/130 |
| 5,155,435 A | * 10/1992 | Kaufman et al. | 324/309 |
| 5,280,427 A | * 1/1994 | Magnusson et al. | 600/407 |
| 5,431,645 A | * 7/1995 | Smith et al. | 606/1 |
| 5,617,874 A | 4/1997 | Baran | 600/558 |
| 5,779,647 A | 7/1998 | Chau et al. | 600/564 |
| 6,022,324 A | 2/2000 | Skinner | 600/566 |
| 6,245,028 B1 | * 6/2001 | Furst et al. | 600/568 |
| 6,283,977 B1 | * 9/2001 | Ericsson et al. | 606/130 |
| 6,331,181 B1 | * 12/2001 | Tierney et al. | 606/130 |

FOREIGN PATENT DOCUMENTS

JP          3121064 A  *  5/1991

OTHER PUBLICATIONS

"CT Fluoroscopy—Guided Abdominal Interventions: Techniques, Results and Radiation Exposure", *Radiology*, Sep. 1999, vol. 201; pp. 576–578.

"Radiation Dosimetry at CT Fluoroscopy: Physician's Hand Dose and Development of Needle Holders", *Radiology*, Nov. 1996, vol. 212; pp. 673–681.

Real–Time CT Chest Biopsies Using a Disposable Stereotactic Imageguided Device, D.S. Sinclair, MD, et al., *RSNA*, Nov. 25–30, 2001.

CT–Integrated Stereotactic Arm for Image–guided Biopsy; Comparison of Speed and Accuracy Using Assisted and Unassisted Methods, E. Kelley, MD, et al., *RSNA*, Nov. 25–30, 2001.

Biopsies under Stereotactic Guidance; Technique and Preliminary Experience, *RSNA*, P. Meingan, MD, et al., Nov. 25–30, 2001.

Initial Experience with a Real–Time Disposable CT Stereotactic Navigator Device for Percutaneous Biopsies, K.K. Vaswani, MD, Ph.D, et al., *RSNA*, Nov. 25–30, 2001.

* cited by examiner

*Primary Examiner*—Kevin Shaver
*Assistant Examiner*—Charles Marmor, II
(74) *Attorney, Agent, or Firm*—Oppenheimer Wolff & Donnelly LLP

(57) ABSTRACT

Remote tissue harvesting and collection apparatuses and methods for their use are disclosed utilizing a remotely controllable tissue harvesting and collection head provided with a reciprocating driving conveyor provided with a tissue collection cannula. These apparatuses and methods provide remote positioning and control of tissue collection cannulas and the subsequent remote tissue harvesting and collection of tissue samples without directly exposing medical personnel to hazardous environmental conditions, including X-rays.

15 Claims, 3 Drawing Sheets

REMOTE TISSUE BIOPSY APPARATUS AND ASSOCIATED METHODS

FIELD OF THE INVENTION

The present invention relates generally to medical instruments that are utilized for obtaining tissue samples from patients. More particularly, the present invention is directed to remote tissue harvesting and collection apparatus and to associated methods of use that are particularly well suited for operation in circumstances where conditions may expose personnel performing the tissue collection to personal hazard from environmental factors, including X-rays.

BACKGROUND OF THE INVENTION

In the course of examining patients, physicians may at times come upon unusual or suspect masses of tissue at various locations throughout the patient's body. For example, these suspect masses of tissue may be located on the body surface of the patient, as well as internally or within particular body organs or structures. Customary medical methods for investigating these suspect masses of tissue include visual inspection, often with aid of magnifying devices, and tactile inspection with the fingers, especially where the suspect mass is internalized within the patient's body. Additional methods for investigating internalized, as well as surface tissue masses, include visualization methods such as X-ray and magnetic resonance imaging (MRI).

Often these methods, either alone or in combination, may not provide enough detailed information about the suspect tissue mass under investigation to allow a physician to diagnose or treat the medical condition associated with the tissue mass. As a result, it is not uncommon for a physician to order a biopsy procedure to be performed on the patient so that the suspect tissues or cells are removed from the patient and then examined in greater detail. The sample of suspect tissue may be obtained by several commonly practiced methods using a variety of medical instruments and tools. These methods include obtaining a tissue plug from the patient's body with a cannula, aspiration of suspect tissue through a needle, swabbing the suspect tissue with a sponge, scraping suspect tissue with a curette, boring into suspect bone tissue with a trepan, or excision of the suspect tissue with a forceps or electric snare, for example. Often the biopsy tissue sample is taken from the edge of the suspect area so as to obtain a sample that contains both healthy and diseased tissue for a more complete tissue comparison and analysis.

The collecting of such tissue samples for biopsy is a standard step in the diagnosis of malignant and benign tumors, as well as other suspect tissues. These tissue biopsies also provide a wide range of other types of diagnostic information, particularly in connection with organs such as the liver or pancreas. By utilizing these methods, a doctor is better able to identify and diagnose a patient and to prescribe the appropriate methods of treatment.

When areas to be biopsied are extracorporeal, or located outside of the patient's body, the initial placement of the prior art medical devices used to extract the samples from the suspect tissues of interest are usually done by hand under direct visualization by the attending medical personnel. However, when the mass of suspect tissue is situated inside of the patient's body, the use of internal visualizing techniques becomes necessary. Without the aid of such techniques, medical personnel conducting the biopsy operation are unable to see the location of internal target areas or, of equal importance, the internal structures that may lie between the point of insertion of the biopsy instruments and their target areas. Without the aid of such prior art enhanced visualization techniques, the medical personnel must insert and guide the biopsy instruments blindly, running the potential risk of impacting healthy tissue located along the intended pathway of the biopsy instrument. Moreover, without such prior art visual aids, it may be possible for the medical personnel to miss the target tissue area entirely, or to over-penetrate the target area and sample tissue outside the target tissue area.

More recently, in an attempt to overcome such visualization obstacles, physicians have been performing biopsies utilizing relatively new methods of enhanced X-ray visualization known as Computed Tomography or "CT". CT allows physicians to obtain a two-dimensional plane view of a cross-section of any part of the patient or targeted internal tissues or organs by combining conventional X-ray technology with modern computers and visual displays. For example, in a CT scan, multiple X-rays are taken as the CT X-ray revolves around the patient placed within the scanning machine. A computer then calculates the amount of X-ray penetration through the specific planes of the body parts examined, and gives each a numeric value known as a "density coefficient". This information is fed into a computer, which translates the density coefficient values into different shades of gray displayed on a television monitor. These displayed images can be presented to the physicians as photographs in a series of two-dimensional photographic images displaying cross-sections of the target areas under examination. When taken as part of a biopsy procedure, these images can be used by the attending medical personnel to visualize both the target areas from which the biopsy samples are to be taken as well as the relative position the biopsy instruments within the patient and the progression of the biopsy instruments along their intended pathways to the suspect masses of tissue at the target areas.

Though successful at helping to direct biopsy instruments, a remaining disadvantage of CT scanning is the fact that the medical personnel performing the biopsy procedures must be mindful of their personal, continued, multiple exposure to the X-ray beam utilized during the CT scanning operations. Failure to do so can lead to the resultant possibility of personal overexposure to X-ray radiation. Overexposure is not an issue to patients due to their relatively brief X-ray exposure. Conversely, medical personnel conducting hundreds of biopsies per year run the risk of significant, cumulative overexposure to X-rays and the subsequent risks to their own health. As a result, this potential for X-ray overexposure requires that any attending medical personnel exit the scan room when the X-ray scanning procedure is taking place. Then, at a later time they can evaluate the CT scan of the area of interest on the patient, analyze the resulting CT images and mark points and decide angles of insertion for biopsy apparatus. Subsequently, in order to advance the biopsy apparatus by moving the tissue sampling instruments deeper into the body, a meticulously slow process follows, consisting of repetitive exits from the scanning room, repetitive CT scans and repetitive image analyses. In between CT scans, the medical personnel advance and adjust the position of the tissue sampling instruments (a cannula, for example), and then scan for the resultant changes in cannula position illustrated by the subsequent CT scans. By using this "still-frame" technique, the progress of the cannula advancing toward the target area is monitored and directed. Though successful, this "still-frame" biopsy visualization methodology is very time consuming and awkward for both patients and attending medical personnel. It is also very expensive and can lead to cost-conscious restrictions on its availability and use.

In view of these drawbacks, continued prior art research has developed an additional method to help medical personnel visualize the interior of biopsy patients in "real-time" as opposed to "still-frame" imaging. "Real-time" imaging enables the medical personnel, with what are essentially "live" images or, in other words, to continuously monitor the target areas of interest. This later method is referred to in the art as "real-time CT fluoroscopy". Utilizing real-time CT fluoroscopy affords medical personnel the ability to generate faster two-dimensional cross-sectional image constructions allowing the target areas to be displayed in "real-time". Medical personnel utilizing this prior art method do not leave the room while the patient is undergoing X-ray scanning. This results in the medical personnel remaining near the X-ray field to manually guide the biopsy instrument's progression to the target tissue in "real-time" using the "real-time" images. While this method provides a continuous, internal view of the patient's target area, the exposure of attending medical personnel to continuous X-rays and the continuing possibility of their personal overexposure to X-rays remains a major concern and limitation on the use of such techniques.

Prior art attempts at reducing radiation exposure and procedure times for medical personnel performing biopsies under "real-time" visualization have relied on simple mechanical solutions akin to removing the medical personnel from the scanning environment. Basically, these techniques involve the medical personnel performing the "real-time" CT fluoroscopy biopsy procedures utilizing simple, passive tools to hold the biopsy instruments. Utilizing a tool such as a set of simple plastic forceps or towel clamps places the hands of medical personnel at approximately 10 cm further away from the X-ray beam. Though effective at reducing X-ray exposure, as one skilled in the art will appreciate, such extending forceps or clamps also position the hands of medical personnel out of direct contact with the patient and biopsy site. Further, such tools also position the biopsy apparatus out of direct contact and control of the attending medical personnel performing the biopsies. The resultant lack of feel, control and stability during the biopsy procedure, combined with the amount of X-ray radiation exposure (3.05 mSV for a 30-second scan at a distance of 10 cm, for example) still associated with such procedures continues to be a source of concern. Additionally, it is extremely difficult, if not impossible, to take biopsy samples from hard tissues such as bone or cirrhotic livers utilizing such forceps or clamp methodologies.

Accordingly, one of the objects of the present invention is to provide remote tissue biopsy apparatuses and associated methodologies that will allow for the accurate and rapid control and positioning of biopsy instruments and for the associated accurate and rapid harvesting of biopsy samples.

An additional object of the present invention is to provide methods and associated apparatuses by which biopsies can be performed under remote control thereby reducing the biopsy conducting medical personnel exposure to hostile environments which may include X-rays, radiation, toxins, pathogens and other hazards.

SUMMARY OF THE INVENTION

These and other objects are achieved by the methods and associated remote tissue biopsy apparatus of the present invention which accurately and rapidly obtain biopsy tissue samples, even in environments that are hostile to medical personnel. In accordance with the broad teachings of the present invention, exemplary remote tissue biopsy apparatus and methods are provided which utilize remotely controllable tissue harvesting and collection heads. These collection heads are provided with a reciprocating driving conveyor having attached a tissue collection cannula. A releasable cannula retaining carrier can be used to attach the tissue collection cannula to the reciprocating driving conveyor. It should be noted that while the present invention will be discussed in the context of biopsy procedures, those skilled in the art will appreciate that the present invention is readily applicable to other tissue harvesting and collection procedures outside of biopsies.

In further accordance with the broad structural aspects and teachings of the present invention, positioning of the remotely controllable tissue harvesting and collection head is further achieved by placing the remotely controllable tissue harvesting and collection head in a mounting fixture for these purposes. An exemplary mounting fixture, for example, may be a component of a handheld unit or of a track mounted robotic apparatus. Further, the remotely controllable tissue harvesting and collection head of the present invention can be connected to the mounting fixture to be spherically pivotable. This provides the apparatus of the present invention additional freedom of motion to allow easier and more precise positioning of the remote controllable tissue harvesting and collection head.

If desired to provide additional structural stabilization to the tissue collection cannula utilized in the present invention, the remote tissue biopsy apparatus of the present invention can include, disposed distally and in axial alignment to the reciprocating driving conveyor, a tissue collection cannula guide. When desired, by providing this tissue collection cannula guide, the present invention further minimizes the amount of flexing and misalignment that may occur between the respective ends of a tissue collection cannula as force is applied to drive the distal end of the tissue collection cannula into the patient undergoing the biopsy procedure.

The remote tissue biopsy apparatus of the present invention can be provided with a remote control that is operatively connected to the remotely controllable tissue harvesting and collection head. This remote control includes an operatively attached tissue harvesting and collection head control mechanism and a user input interface. This enables medical personnel performing a biopsy to actuate and operate the remotely controllable tissue harvesting and collection head from a distance, outside of a X-ray scanning field, for example. In accordance with the teachings of the present invention the tissue harvesting and collection head control mechanism can be, for example, mechanical, pneumatic, electrical or hydraulic mechanisms. These mechanisms can actuate, for example, levers, belts, chains, pistons, cylinders or solenoids that operatively connect the user input interface to the remotely controllable tissue harvesting and collection head.

In an exemplary handheld embodiment of the present invention, the user input interface is mechanical, structurally simple and disposed at a handle portion of the apparatus provided in accordance with the teachings of the present invention.

To collect or harvest suspect tissue of interest in accordance with the teachings of the present invention, the tissue harvesting and collection head is maneuvered to a predetermined location on the patient. This location can be predetermined and previously marked by medical personnel based on visualization, palpation or images from earlier scans of the target tissue. Then, while the CT fluoroscope is turned on and a cross-sectional image is constructed of the patient's internal target tissue area, the medical personnel evaluate this visual image and position the remote tissue biopsy apparatus accordingly. This is accomplished manually if the embodiment of the present invention employed is handheld, or mechanically if an embodiment of the present invention is robotic. The medical personnel are then able to actuate and guide the remotely controllable tissue harvesting and collection head to the target tissue to be biopsied by utilizing the user interface of the remote tissue biopsy apparatus while continuously monitoring the images constructed by the scanner. This remote tissue biopsy apparatus and technique enables the medical personnel to adjust, in "real-time", the aim and progression of the tissue collecting instruments toward the target areas.

Moreover, as will be appreciated by those skilled in the art, the exemplary remote tissue biopsy apparatus of the present invention is lightweight and can be handheld or robotic. An exemplary handheld remote tissue biopsy apparatus of the present invention has a "gun-like" appearance, in that the remotely controllable tissue harvesting and collection head can be disposed distally from a "pistol-grip" member. The pistol grip contains the user input interface that is operatively linked to the remote control mechanism, in this embodiment, disposed within the handheld remote tissue biopsy apparatus.

Alternatively, at least a portion of exemplary remote tissue biopsy apparatus of the present invention can be manufactured as a disposable unit and, as such, can be constructed of appropriately robust yet inexpensive materials. Whether disposable or not, a handheld remote tissue biopsy apparatus may be proportioned so as to fit within confined areas, such as a CT apparatus or otherwise restrictive areas. Additionally, within the scope and teachings of the present invention, the handheld remote tissue biopsy apparatus are of sufficient extending length to distance the medical personnel for protection from X-rays associated with CT procedures or from other hazards such as heat, toxins, energy fields or biohazards. Alternatively, within the teachings of the present invention, a handheld remote tissue biopsy apparatus also can provide shielding, such as lead, incorporated into the design and materials utilized in the construction of the handheld remote tissue biopsy apparatus in order to further minimize the user's exposure to radiation or other detrimental elements.

In further accordance with the novel structural aspects of the present invention, the mounting fixture can be part of a remote control, robotic apparatus. Such robotic apparatus of the present invention can be similar to robots found in modern automated assembly lines. Such exemplary robotic apparatus of the present invention can mount the tissue harvesting and collection head on robotic positioning and extension arms disposed on a track. This robotic positioning and extension arm allows accurate three-dimensional remotely controlled positioning of the tissue harvesting and collection head through points in the x, y, and z planes.

The remotely controllable robotic apparatus of the present invention allows medical personnel to obtain biopsy samples from both hard and soft tissues with precision, control and safety, without any direct physical contact between the medical personnel conducting the biopsy procedures and the patients. This apparatus and methods of the present invention are equally adaptable to other medical devices, such as CT fluoroscopes or even to portable platforms for ease of transport and for use in remote locations.

The following non-limiting detailed description and drawings, which illustrate, by way of example, the principles of the present invention, will provide additional enabling disclosure and examples and will make apparent additional features and advantages of the present invention to those skilled in the art.

DETAILED DESCRIPTION OF EXEMPLARY EMBODIMENTS

Figure 1:
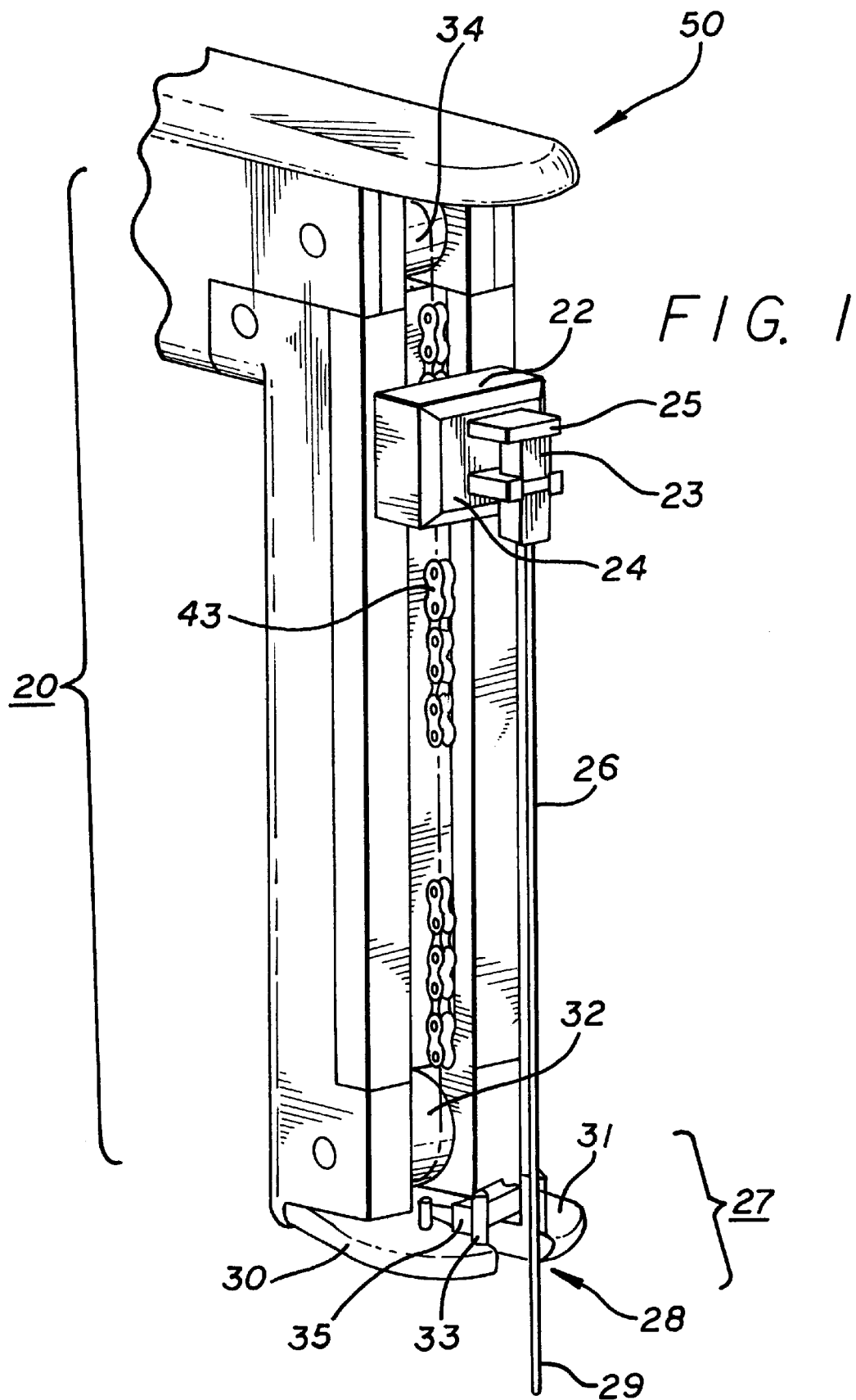
FIG. 1 is a perspective view of an exemplary remotely controllable tissue biopsy harvesting and collection head illustrating the principles of the present invention.

The remote tissue biopsy apparatus and associated methods of the present invention are used in medical procedures that require the harvesting of tissues from patients under study. These target tissues may be present at any location on or within a patient's body. For example, targeted or suspect masses of tissue to be biopsied may be found either outside or inside a patient's body cavity. In accordance with the teachings of the present invention, placement of the tissue harvesting apparatus and subsequent harvesting of the target tissues are accomplished both expeditiously and accurately with minimal inconvenience to the patients undergoing biopsy procedures. At the same time, the present invention affords the medical personnel conducting the tissue harvesting to do so safely, outside of hostile environments while maintaining the precision and control necessary to successfully harvest the targeted tissues. The apparatus and methods of the present invention also permit biopsy procedures to be executed under remote control, thus affording medical personnel the ability to gather and sample tissue specimens from patients without direct physical contact with the patients. These previously unobtainable features and advantages provided by the present invention are significant improvements over the prior art methods of harvesting tissue samples.

Currently many biopsy procedures generally can last from 15–45 minutes. The present invention can significantly reduce these time periods. Prior art X-ray and CT methodologies have developed set accepted standards of personal radiation exposure for medical personnel and patients alike. In these prior art methodologies the hands of medical personnel performing such prior art, "real-time" CT biopsy procedures generally are exposed to 3.05 mSv of radiation while the neck and bodies of the medical personnel are exposed to 0.015 mSv of radiation during a single 90 second span. These industry standard, minimally acceptable levels of personal radiation exposure are commensurate with prior art real-time CT scan biopsy procedures utilizing a 10 cm plastic forceps to handle the tissue collection cannula at a safe distance during the prior art biopsy procedures. The apparatus and methods of the present invention significantly reduce these levels of personal radiation exposure while improving precision or control. In fact, utilizing the apparatus and methods of the present invention enables medical personnel to harvest tissue samples from small target tissues.

It should be noted that the remote tissue biopsy apparatus of the present invention can be constructed of non-radiopaque materials so as to not obscure desired X-ray image construction and visualization. Additionally, at least some portions of the apparatus of the present invention may require sterilization. As such, in accordance with the teachings of the present invention materials used should be able to withstand standard sterilization techniques without damage, distortion, or loss of material integrity or function.

The apparatus and methods of the present invention involve human input or control of the remote tissue biopsy apparatus. Human input and control of the present invention during biopsy procedures is an aspect of the present invention that physicians and medical personnel desire in medical devices. The present invention provides such desirable input interfaces and assures widespread acceptance of the present invention's remote tissue biopsy apparatus in the medical community. However, alternative embodiments may involve automated target location and tissue sampling via computer assisted imaging and robotic commands to the remote tissue biopsy apparatus. Further adding to this desired human input and control, another important aspect of the present invention is the positioning, control, and maneuverability of the remote tissue biopsy apparatus. In accordance with the teaching of the present invention, exemplary remote tissue biopsy apparatus are provided with tissue harvesting and collection heads that can spherically pivot or move along three coordinate axes as well as pivoting through at least + or −30° pitch and yaw angles. This greatly facilitates tissue harvesting and collection procedures utilizing the present invention relative to conventional prior art clamp tools and techniques. Further adding to the desirability and medical acceptance of the present invention is the ability of the apparatus of the present invention to be mobile and set up for use expeditiously. Moreover, the present invention is adaptable and can be utilized with any standard X-ray or CT scanner or the like. The present invention also is compatible with a wide variety of shapes and sizes of conventional tissue collection cannulas.

Turning now to the drawings, as illustrated in FIG. 1, an exemplary remotely controllable tissue harvesting and collection head 20 of the present invention includes a reciprocating driving conveyor 22 in connection with remotely controllable tissue harvesting and collection head 20, and a tissue collecting cannula 26 attached to reciprocating driving conveyor 22. Tissue collection cannula 26 can be releaseably attached to reciprocating driving conveyor 22. Alternatively, tissue collection cannula 26 and reciprocating driving conveyor 22 may be a one piece unit.

Additionally, remotely controllable tissue harvesting and collection head 20 is attached to mounting fixture 50. Mounting fixture 50 is configured to impart a degree of spherical pivotability to remotely controllable tissue harvesting and collection head 20 relative to mounting fixture 50. Such spherical pivotability may be provided by a ball and socket type joint as well as other pivotable joint types. This structural arrangement provides the apparatus of the present invention with the ability to position tissue harvesting and collection head 20 at virtually any point in the x, y, and z-axes relative to the spherical space defined by remotely controllable tissue harvesting and collection head 20 relative to mounting fixture 50 and, ultimately, relative to the biopsy patient and scanning machine X-ray field (not shown).

Figure 2:
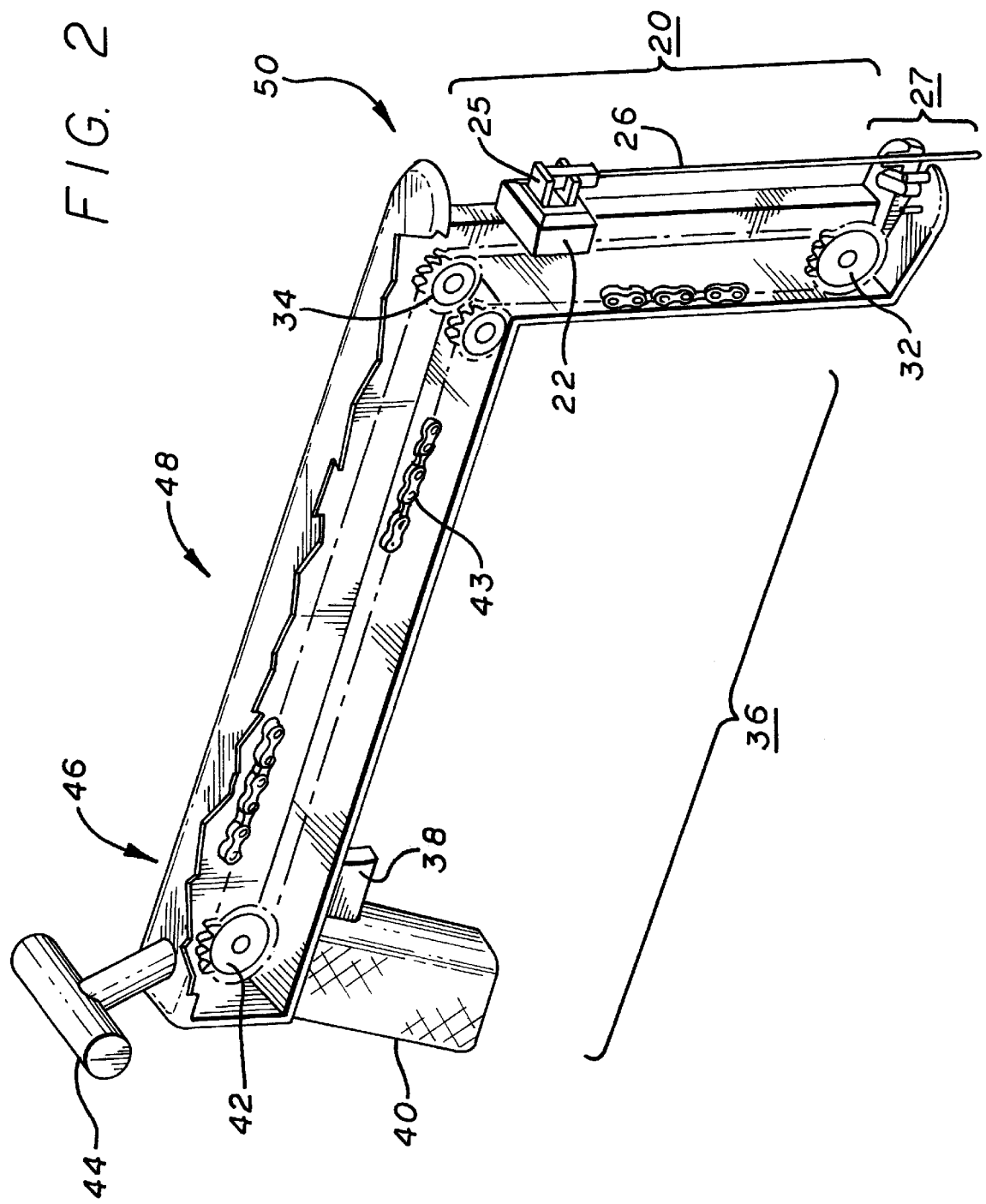
FIG. 2 is a cut-away perspective view of an additional alternative embodiment illustrating additional features of the present invention.

As shown in FIGS. 1 and 2, a cannula retaining carrier 24 can be attached to the anterior facing side of reciprocating driving conveyor 22 to hold a tissue collection cannula hub 23 or a variety of cannula types, such as trocar, core, fine as well as others. In the exemplary embodiments shown, cannula retaining carrier 24 and reciprocating driving conveyor 22 are constructed as a single element. In accordance with the teachings of the present invention, cannula retaining carrier 24 may also be fixedly attached or detachable from any face of reciprocating driving conveyor 22 providing medical personnel the ability to change types of cannula retaining carriers 24 where carriers are constructed to hold only one type of tissue collection cannula 26. Alternatively, cannula-retaining carrier 24 can incorporate a "universal" mount which is able to hold a variety of different tissue collection cannula hubs 23. Universal mount 25 on cannula-retaining carrier 24 is provided with extensions by which the different types of tissue collection cannulas 26 may be held at hub 23 through snap-fit, frictional engagement, interlocking threads or other methods as known in the art.

In exemplary embodiments, tissue collection cannula 26 has a hollow interior and hub 23 at the proximal end and tip 29 at the distal end. Typically, tissue collection cannula 26 is inserted into the patient to the appropriate depth for the target tissue site.

An optional element of remotely controllable tissue harvesting and collection head 20 is a tissue collection cannula guide 28, disposed near the distal end 27 of remotely controllable tissue harvesting and collection head 20. As tissue collection cannula 26 is inserted into the patient undergoing the biopsy procedure, cannula tip 29 may encounter resistance as it punctures and or cores into the tissue. Tissue collection cannula guide 28 provides tissue collection cannula 26 with stabilizing support at tip 29. The opposing halves 30 and 31 of tissue collection cannula guide 28 are shown in an open position, illustrating how tissue collection cannula 26 is threaded therethrough in axially-stable sliding engagement (FIG. 1). When tissue collection cannula 26 is mounted in axial alignment with reciprocating driving conveyer 22, the halves 30 and 31 are brought together and secured in place around tissue collection cannula 26 by a releasable latch 35. Tissue collection cannula guide 28 is dimensioned as to appropriately accommodate the intended variety of cannula gauges and configurations. For example, accommodation of a particular tissue collection cannula diameter or gauge is achieved by varying the diameter of the guiding sleeve 33. Alternatively, removable bushings of varying diameter may be used within guiding sleeve 33 to alter its diameter. Alternative methods of accommodation include the use of pliable, form-fitting materials, such as rubberized foam, to form guiding sleeve 33 through which tissue collection cannula 26 passes. Similarly, if desired, tissue collection cannula guide 28 may be configured to be detachable from distal end 27 of remotely controllable tissue harvesting and collection head 20, so that guiding sleeve 33 with the appropriate dimensions to accommodate and support a particular cannula may be substituted.

As further illustrated in FIG. 1, the exemplary embodiment permits reciprocating driving conveyor 22 which linearly travels along the vertical axis of tissue harvesting and collection head 20. Reciprocating driving conveyor 22 can be slidably attached to the body of remotely controllable tissue harvesting and collection head 20. This arrangement can be achieved by providing vertical slots (not shown) that run essentially the length of remotely controllable tissue collection and harvesting head 20 within which tabs on the posterior facing side of reciprocating driving conveyor 22 slide. Alternative reciprocating driving conveyor 22 guiding arrangements as known in the art are contemplated as being within the scope of the present invention.

As those skilled in the art will appreciate, the particular environment where the tissue harvesting and collection will be performed, as well as the type of biopsy procedures called for can determine the overall length and relative dimensions of remotely controllable tissue harvesting and collection head 20 as well as that of tissue collection cannula 26 and the entire remote tissue biopsy apparatus. The materials and dimensions of exemplary remotely controllable tissue harvesting and collection head 20 are configured to minimize radiation exposure to the medical personnel performing the tissue collection procedure (utilizing real-time CT fluoroscopy, for example) or to distance medical personnel from harmful environments. For example, in accordance with the teachings of the present invention, minimization of radiation exposure can be accomplished by positioning remotely controllable tissue harvesting and collection head 20 on a handheld mounting fixture 50 of any length appropriate to position the medical personnel outside of the radiation field. In one exemplary embodiment, it is contemplated to be within the scope of the present invention to provide a handheld mounting fixture 50 with a length greater than or less than 30 cm, as dictated by the operating environment. Alternatively, it is considered to be within the scope of the present invention that mounting fixture 50 can be part of a robotic system that removes medical personnel from the radiation field. Similarly, sampling tissues located at differing depths within a body cavity can require cannulas of differing lengths or reciprocating driving conveyor strokes of different lengths. Likewise, as known in the art, cannula or needle types may be predicated upon the type of tissue to be harvested.

FIG. 2 further illustrates an alternative embodiment of the present invention configured as a handheld remote tissue biopsy apparatus generally indicated by reference numeral 36. Remotely controllable tissue harvesting and collection head 20 is attached at mounting fixture 50, shown here without the spherical range of movement.

A remote control allows for the movement of reciprocating driving conveyor 22 to be effectuated from a distance. Further, tissue harvesting and collection head control mechanism elements connected between the user input interface and remotely controllable tissue harvesting and collection head 20 are employed to position reciprocating driving conveyor 22.

As further illustrated in FIG. 2, mounting fixture 50 is disposed at the end of a longitudinal body member 48. Longitudinal body member 48 may be of sufficient length to place the attending medical personnel at safe distances that minimize their exposure and contact with hazards, for example X-rays utilized in "real time" CT fluoroscopy.

Additionally, handle member 40 is provided for accurate and precise positioning and control of remotely controllable tissue harvesting and collection head 20 and tissue collection cannula 26. Further, remote control of the movement of reciprocating driving conveyor 22 is provided by a user input interface, here an actuating trigger 38, which operatively contacts and actuates the movement of a drive chain 43, over gears 34 and 32, for example, moving reciprocating driving conveyer 22 a precise, controllable distance under precise, controllable, manually applied pressure to actuating trigger 38. Remote control of the movement of remotely controllable tissue harvesting and collection head 20 and tissue collection cannula 26 can be alternatively be provided by other user input interfaces such as push pads, levers and other devices as known in the art.

As further illustrated in FIG. 2, movement of reciprocating driving conveyer 22, is achieved by a variety of drive mechanisms. In the exemplary embodiment of FIG. 2, reciprocating driving conveyor 22 is operatively attached to a drive chain 43 that is part of a chain drive mechanism that is situated within handheld remote tissue biopsy apparatus 36. Operatively attaching reciprocating driving conveyor 22 to the chain drive mechanism can be achieved by, including but not limited to, pins, screws, nuts, bolts, rivets, glues, and welded seams.

In order to move reciprocating driving conveyor 22, actuating trigger 38 is squeezed posteriorly, that is, toward handle member 40, and actuating trigger 38 engages a drive chain 43 directly or indirectly. This rearward, linear movement of actuating trigger 38 is translated by drive chain 43 through gears 42, 34 and 32, respectively. As reciprocating driving conveyor 22 is operatively attached to drive chain 43, the drive chain's movement will result in reciprocating driving conveyor 22 moving towards the patient with sufficient force to penetrate tissue. This penetrating force can be controllable by proportionate pressure to actuating trigger 38 by the attending medical personnel. Approximately 3 to 5 pounds of force are maximally required for actuating the movement of actuating trigger 38 or gear 42.

Forward movement of actuating trigger 38, upon release of the rearward pressure is achieved, for example, by a spring mechanism such as a coil or leaf type spring. The release of actuating trigger 38 disengages actuating trigger 38 directly or indirectly from drive chain 43. With actuating trigger 38 thus disengaged, the rotation of gear 42, either clockwise or counter-clockwise, moves reciprocating driving conveyor 22 relative to mounting member 50. Use of a manually accessible knob, for example, operatively connected to gear 42, or multiple gears is desirable because it provides force feedback sensation to medical personnel, allowing a better "feel" for the tissue through which tissue collection cannula 26 is travelling. In addition to actuating trigger 38 effecting the movement of drive chain 43 disclosed herein, mechanisms utilized to drive the movements of reciprocating driving conveyor 22 can also include, but not be limited to, other mechanical, electric, hydraulic, and pneumatic means coupled to levers, gears, rods, clutches, belts and linkages, for example.

The exemplary handheld remote tissue biopsy apparatus 36 are successfully utilized in 30 "real-time" CT fluoroscopy protocols because materials utilized in its construction may be non-radiopaque. This is a desirable feature so that the remote biopsy apparatus may be used in proximity of a scanning X-ray plane, yet not contribute or interfere with the images resulting from scanning procedures. Representative examples of plastic materials that display this feature include polyformaldehydes, polycarbonate, polyamides and polypropylenes, though alternative materials are contemplated.

Additionally, materials chosen to comprise parts of exemplary handheld remote tissue biopsy apparatus 36 of the present invention which will come into contact with the patient, tissue collection cannula 26 or medical personnel during the biopsy procedure, may preferably be able to withstand current methods of sterilization without distortion or loss of physical integrity. In exemplary embodiments, Deralin™, a polyformaldehyde, can be used for fabrication of handheld remote tissue biopsy apparatus 36 because of its machinability, durability and resistance to distortion under extreme sterilization temperatures.

In accordance with the teaching of the present invention, this exemplary handheld remote tissue biopsy apparatus 36 is constructed to be non-bulky, balanced, and relatively lightweight. This construction provides ease of use, while minimizing fatigue. As a result, it is possible to provide and maintain a relatively high degree of accuracy and precision in harvesting and collecting the targeted suspect tissues. In exemplary embodiments, handheld remote tissue biopsy apparatus 36 can weigh between about 1 to 4 pounds, preferably between 1.3 pounds and 1.8 pounds and is about 7 to 10 inches long and 1.5 to 2.4 inches wide or greater.

Handle member 40 should not be of too great a length to interfere with the medical personnel's ability to maneuver handheld remote tissue biopsy apparatus 36. Handle member 40 that extends too far results in the medical personnel possibly pressing handle member 40 onto the patient when shallow angles of tissue collection cannula 26 insertion are called for, thus imposing a limit to the angle of insertion available to the medical personnel.

As illustrated in FIG. 2, a dorsal handle member 44, disposed at the top, or dorsal portion 46 of handheld remote tissue biopsy apparatus 36 can be provided. Dorsal handle member 44 provides an increase in the overall stability of handheld remote tissue biopsy apparatus 36 and aids in supplying downward force when the penetration of hard tissue is necessary, by allowing the medical personnel to position and control the apparatus with both hands while controlling actuating trigger 38 with one hand independent of the other hand.

An optional measure of safety is realized by the placement of a marking onto the posterior portion of the device to indicate a "radiation safe" zone when exemplary devices are utilized in procedures that may expose medical personnel to radiation fields.

Figure 3:
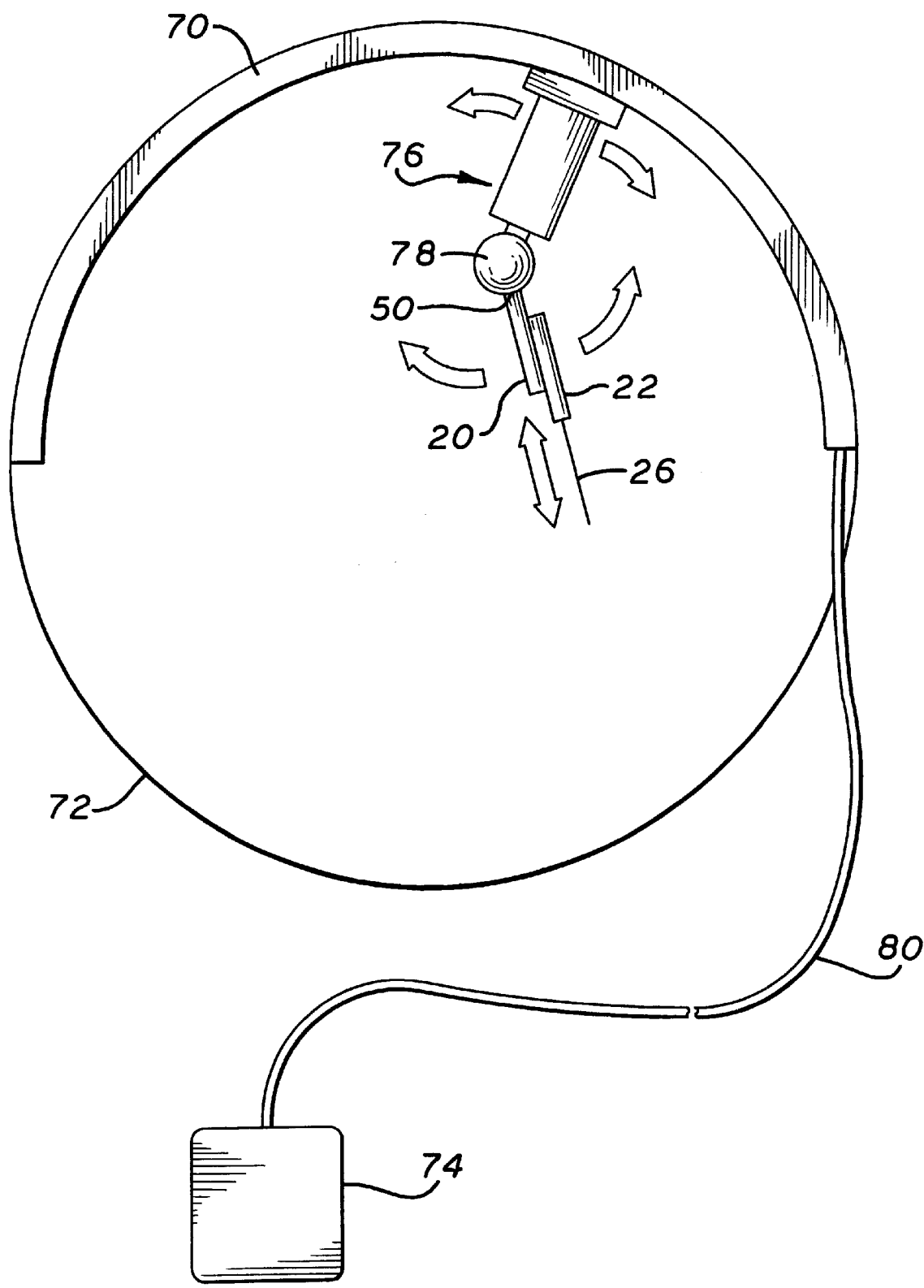
FIG. 3 is a plan view of an alternative exemplary embodiment of a remotely controllable robotic tissue harvesting and collection head illustrating additional features of the present invention.

An alternative robotic embodiment in accordance with the teachings and methods of the present invention is illustrated in FIG. 3. Here remotely controllable tissue harvesting and collection head 20, is attachable to mounting fixture 50 that is comprised of a robotic positioning and extension arm 76 disposed upon a track 70 and gantry 72. Robotic positioning and extension arm 76 can be movable. It is also contemplated that robotic positioning and extension arm 76 can also be a non-moveable aspect fixed to a device such as a CT fluoroscope or other platform, for example. Furthermore, it is considered to be within the scope of the present invention to have robotic positioning and extension arm 76 outside of a medical imaging device, such as a CT fluoroscope, and be controllably projected into the CT fluoroscope. The user input interface 74 in this embodiment is operatively connected 80 to the remotely controllable tissue harvesting and collection head 20. User input interface 74 can be hardwired to robotic remote tissue biopsy apparatus. It is within the scope of the present invention that user input interface 74 may also send commands from medical personnel wirelessly as well as transmit commands over distances by utilizing video and satellites to allow visualization of the procedure and provide control of the remote tissue biopsy apparatus from virtually anywhere. For example, this ability is possible with the increase in utilization and capability of the Internet in the medical profession Medical personnel in one location will be able to perform biopsies at remote locals without ever having to venture to the biopsy procedure site.

To utilize this embodiment with CT fluoroscopy, the patient is placed within the CT fluoroscope wherein robotic positioning and extension arm 76 is located. The medical personnel, utilizing user input interface 74, then actuates the robotic positioning and extension arm 76 to manipulate the position of reciprocating driving conveyor 22. Also, user input interface 74 may be operated to move reciprocating driving conveyor 22 relative to tissue harvesting and collection head 20 and into, or out of, the tissue. Robotic positioning and extension arm 76, being mounted on track 70 and gantry 72, moves to the target insertion site, which is located at a particular x, y, and z point, previously selected by the medical personnel. Track 70 and gantry 72 provide robotic positioning and extension arm 76 a wide range of movement. This range of movement and angle of tissue collection cannula 26 insertion is augmented by the utilization of joint 78 at a point or points along robotic positioning and extension arm 76.

Movement of reciprocating driving conveyor 22 as well as robotic positioning and extension arm 76 may be effectuated by remote control mechanisms and include, but are not limited to, mechanical, electric, pneumatic and hydraulic means of actuating levers, chains and gears.

Considerations regarding appearance, materials and operation are also areas of concern for the robotic embodiment of the present invention. Procedures utilized to address these concerns in regards to the handheld embodiment are likewise applicable to the robotic embodiment. Further, remotely controllable tissue harvesting and collection head 20 can be a disposable unit, quickly detachable and replaced onto robotic positioning and extension arm 76.

User input interface 74 and automation of positioning remotely controllable tissue harvesting and collection head 20 by remote control is a vast improvement over prior art methodologies. The teachings and methods of the present invention allow medical personnel to perform "real-time" biopsy procedures including utilizing a CT fluoroscope as well as other visualization techniques, without having direct contact with the patient. When such procedures are carried out in a hospital setting, medical personnel perform the biopsy procedure in a separate room or at such distance from the CT fluoroscope that their exposure to X-rays is negligible. This reduction to radiation exposure alleviates the former concern of medical personnel to the damage of cumulative exposure to radiation associated with the prior art methodologies.

In addition to the previously cited example of performing "real-time" biopsies utilizing a CT fluoroscope and the radiation hazards associated with the technique, there are additional situations that require the remote sampling of tissues. For example, at sites where radiation leakage is thought to have occurred, a mobile remote control vehicle or robotic unit, much like those utilized currently by demolition squads to handle explosive devices, can be modified to carry robotic positioning and extension arm 76 with attached remotely controllable tissue harvesting and collection head 20. Such a device is sent into the hazardous area and able to sample tissues of potential victims of exposure.

Hazardous conditions are not only limited to radiation but can also include biohazards, toxic chemicals and other various detrimental conditions. Such conditions can occur at industrial manufacturing and storage facilities as well as other locales. A remote tissue biopsy apparatus within the scope of the teachings of the present invention provides a valuable means of remotely sampling potentially exposed personnel.

A further understanding of the present invention will be accorded to those skilled in the art from a consideration of the following non-limiting example. This example illustrates the utilization of a remote tissue biopsy apparatus under hazardous conditions. It is emphasized that this example is illustrative of the principals and teachings of the present invention and is not intended to limit the scope of the invention to exemplary remote tissue biopsy apparatuses alone.

EXAMPLE

In accordance to the teachings utilizing the present invention a functional tests were carried out of a remote tissue biopsy apparatus configured as the exemplary handheld apparatus illustrated in FIGS. 1 and 2. Basic testing shows that utilization of a chain drive mechanism and manually actuating trigger 38 in contact with the drive chain 43 results in about 5.5 lbs. of force deliverable to the tissue collection cannula tip 29. The exemplary distance of actuating trigger 38 travel is 2 cm when depressed. The handheld apparatus weighed 1.31 pounds and the tissue collection cannula 26 traveled in a defined path, thereby minimizing peripheral tissue destruction.

Tissue harvesting and collection procedures in accordance with the teachings of the present invention were performed on samples chosen to simulate human skin as well as muscle, bone and fatty tissue (grapefruit and pork roast).

Small targets (plastic chain links) were inserted into the grapefruit to simulate suspect tissues. The grapefruit was placed in a CT scanner and the plane containing the target, was generated and visualized. Using a computer screen upon which "real-time" images of the target in the sample were shown, the handheld apparatus exemplary of the teaching of the present invention was positioned against the surface of the grapefruit and the actuating trigger 38 pulled, driving tissue collection cannula 26 into the sample. Tissue collection cannula 26 was guided to the target tissue (plastic chain link)in a matter of seconds.

Trials with both samples were successful in locating and expeditiously reaching the target. The exemplary handheld remote tissue biopsy apparatus 36 of the present invention was very easy to control and master, kept the medical personnel's hands within safe radiation distance while the "tissue harvesting" was performed. The chain drive mechanism successfully translated the horizontal trigger motion to vertical motion, driving the tissue collection cannula into the target.

It is to be understood that the embodiments of the invention disclosed are illustrative of the principals of the invention. Other modifications may be employed which are within the scope of the invention. Thus, different tissue harvesting and collection head control mechanisms may include, by way of example but not limitation, straight linkages with various bell cams and pivots. Additionally, pneumatic control mechanisms may be provided with a piston/cylinder pressurized assembly. Alternatively, chemically activated control mechanisms utilizing chemicals similar to those currently deployed in vehicular air bags are further contemplated. Accordingly, the present invention is not limited to that precisely shown and described in the present specification.

We claim:

1. A handheld remote tissue biopsy apparatus comprising:
   a longitudinal body having a proximal end and a distal end;
   a handle depending from said proximal end of said longitudinal body;
   a tissue harvesting and collection head having a reciprocating driving conveyor disposed adjacent said distal end of said longitudinal body; and
   a tissue collection cannula attached to said reciprocating driving conveyor.

2. The apparatus of claim 1, further comprising a cannula retaining carrier attached to said reciprocating driving conveyor.

3. The apparatus of claim 2, further comprising a tissue collection cannula guide, distally disposed from said cannula retaining carrier and in axial alignment with said tissue collection cannula and said reciprocating driving conveyor.

4. The apparatus of claim 1, wherein said reciprocating driving conveyor is mechanical.

5. The apparatus of claim 1, wherein said reciprocating driving conveyor is pneumatic.

6. The apparatus of claim 1, wherein said reciprocating driving conveyor is electrical.

7. The apparatus of claim 1, wherein said reciprocating driving conveyor is hydraulic.

8. The apparatus of claim 1, further comprising an actuating trigger disposed adjacent said handle and driving a chain manipulating said reciprocating driving conveyor.

9. A method for performing a tissue harvesting and collection procedure in conjunction with real time fluoroscopic computed tomography, said method comprising the steps of:
   positioning a patient in a fluoroscopic computed tomography scanner;
   operating said fluoroscopic computed tomography scanner to visualize a target tissue within said positioned patient;
   utilizing said handheld remote tissue biopsy apparatus of claim 1 to direct said tissue collection cannula into said target tissue to collect a sample of said target tissue within said tissue collection cannula; and
   harvesting said sample from said tissue collection cannula.

10. The method of claim 9, wherein said handheld remote tissue biopsy apparatus is made from non-radiopaque material.

11. The method of claim 10, wherein the apparatus further comprises a cannula retaining carrier releasably attached to said reciprocating driving conveyor.

12. The method of claim 11, wherein the apparatus further comprises a tissue collection cannula guide, distally disposed from said cannula retaining carrier releasably attached to said reciprocating driving conveyor and in axial alignment with said tissue collection cannula and said reciprocating driving conveyor.

13. A handheld remote tissue biopsy apparatus comprising:
   a longitudinal body having a proximal end and a distal end;
   a handle depending from said proximal end of said longitudinal body;
   a tissue harvesting and collection head having a reciprocating driving conveyor disposed adjacent to said distal end of said longitudinal body;
   an actuating trigger disposed adjacent said handle;
   a drive mechanism operatively connected to said actuating trigger for manipulating said reciprocating driving conveyor; and
   a tissue collection cannula attached to said reciprocating driving conveyor.

14. The apparatus of claim 13, wherein said proximal end of said longitudinal body is provided with a stabilizing handle.

15. The apparatus of claim 13, wherein said drive mechanism is a drive chain connected from said actuating trigger to said reciprocating driving conveyer.

* * * * *